US009914075B1

(12) United States Patent
Palumbo

(10) Patent No.: US 9,914,075 B1
(45) Date of Patent: Mar. 13, 2018

(54) TURBIDITY MEASURING DEVICE

(71) Applicant: TINTOMETER, GMBH, Dortmund (DE)

(72) Inventor: Perry Palumbo, Fort Collins, CO (US)

(*) Notice: Subject to any disclaimer, the term of this patent is extended or adjusted under 35 U.S.C. 154(b) by 39 days.

(21) Appl. No.: 15/129,201

(22) PCT Filed: Jun. 3, 2016

(86) PCT No.: PCT/US2016/035638
§ 371 (c)(1),
(2) Date: Sep. 26, 2016

(87) PCT Pub. No.: WO2016/200680
PCT Pub. Date: Dec. 15, 2016

Related U.S. Application Data

(60) Provisional application No. 62/173,101, filed on Jun. 9, 2015, provisional application No. 62/174,243, filed on Jun. 11, 2015, provisional application No. 62/244,004, filed on Oct. 20, 2015, provisional application No. 62/315,298, filed on Mar. 30, 2016.

(51) Int. Cl.
| | | |
|---|---|---|
| *G01N 21/47* | (2006.01) | |
| *B01D 19/00* | (2006.01) | |
| *G02B 5/04* | (2006.01) | |
| *G01N 15/06* | (2006.01) | |
| *G01N 21/53* | (2006.01) | |

(52) U.S. Cl.
CPC ......... *B01D 19/0042* (2013.01); *G01N 15/06* (2013.01); *G01N 21/534* (2013.01); *G02B 5/04* (2013.01)

(58) Field of Classification Search
CPC .......... G01N 15/0205; G01N 15/1434; G01N 15/1436; G01N 15/1459; G01N 21/51; G01N 21/53; G01N 21/532
USPC .......... 356/246, 432–440, 335–343
See application file for complete search history.

(56) References Cited

U.S. PATENT DOCUMENTS

| | | | |
|---|---|---|---|
| 2,535,181 A | 12/1950 | Way | |
| 3,333,414 A | 8/1967 | Saintsbury | |
| 3,831,907 A * | 8/1974 | Claes | B01F 3/088 366/172.1 |
| 3,926,654 A * | 12/1975 | Claes | B01F 3/088 106/156.2 |
| 4,690,560 A * | 9/1987 | Coogan | G01N 21/51 356/236 |
| 4,906,260 A | 3/1990 | Emheiser et al. | |
| 5,674,200 A | 10/1997 | Ruschke et al. | |
| 2010/0002229 A1 | 1/2010 | Larsen et al. | |
| 2012/0182554 A1 | 7/2012 | Nyhart, Jr. | |

* cited by examiner

*Primary Examiner* — Hoa Pham
(74) *Attorney, Agent, or Firm* — Leyendecker & Lemire, LLC

(57) ABSTRACT

Embodiments of the present invention can include a turbidity measuring device. Typically, the turbidity measuring device can include a fluidic module and a measurement module. The measurement module can removably couple to the fluidic module and be implemented to measure a turbidity of a liquid passing through the fluidic module. The fluidic module can include a sub-assembly that can form a deaerator within the fluidic module. In one instance, the deaerator can be implemented to separate entrained air and/or other gases from a continuous flow of liquid by means of nucleation before the liquid is assayed.

23 Claims, 15 Drawing Sheets

US 9,914,075 B1

TURBIDITY MEASURING DEVICE

CROSS-REFERENCE TO RELATED APPLICATIONS

This application claims the benefit of U.S. Provisional Application No. 62/173,101, filed Jun. 9, 2015, U.S. Provisional Application No. 62/244,004, filed Oct. 20, 2015, U.S. Provisional Application No. 62/174,243, filed Jun. 11, 2015, and U.S. Provisional Application No. 62/315,298, filed Mar. 30, 2016.

FIELD OF THE INVENTION

The present invention relates to a removal of one or more entrained interferences including, but not limited to, air and other gases from a continuous stream of liquid prior to an assay process. The assay process can be implemented to determine turbidity, color, chemical constituents, and/or physical properties of the liquid thereof.

BACKGROUND

A determination of a constituent of a liquid sample flowing in a stream may be carried out using a variety of methods and techniques. A significant number of methods and analysis techniques rely on interrogating the liquid sample using optical means. Optical means is where a beam of light, or other electromagnetic radiation, is transmitted through the liquid and the light is either absorbed or scattered or the light stimulates fluorescence in proportion to a determinable component of the liquid, analyte, or contaminate of interest.

Entrained air and other gases present within the liquid sample can cause a portion of the light beam to scatter as the light travels through the liquid sample resulting in a reduced transmission of the light through the liquid sample. Entrained air and other gases also increase an observability of the beam within the liquid. The decrease in the transmission of light through the liquid sample due to entrained air mimics absorption and is indistinguishable from that which is due to an analyte. The observability of the beam due to entrained air likewise interferes with nephelometric or fluorometric determination methods as more light is scattered than can be accounted due to particle content or fluorescence of the liquid sample.

It is therefore important for an accurate determination of a constituent of a liquid that air or other entrained gases be removed prior to interrogation of the liquid sample by a beam of light. More specifically, air or other entrained gases should be (i) removed to the extent that the remaining air or gases have no significant contribution to a limit of detection of the method of analysis, and/or (ii) reduced to less than that which does not interfere with a determinable property of the liquid.

DETAILED DESCRIPTION

Figure 1:
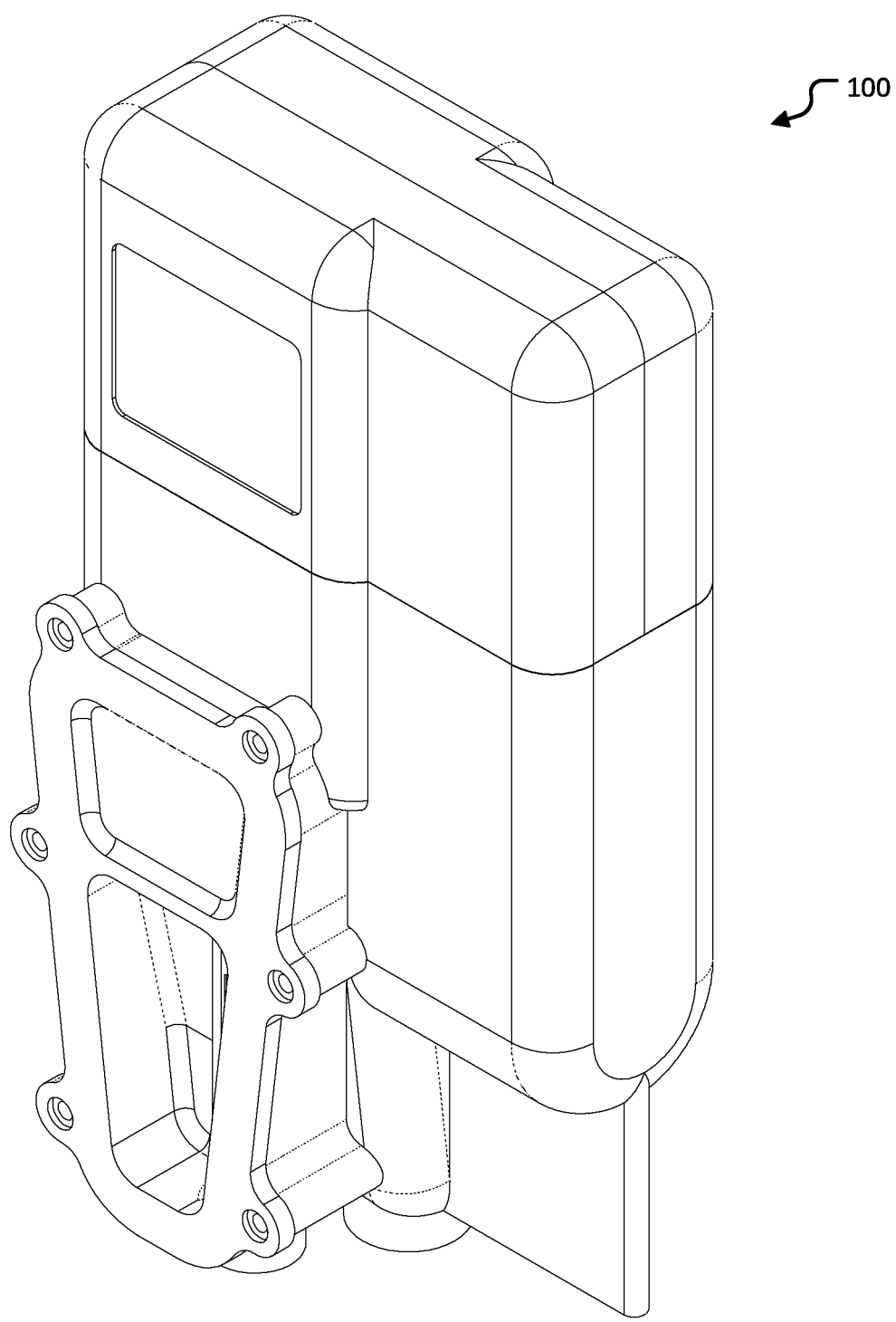
FIG. 1 is an isometric view of a turbidity measuring device according to one embodiment of the present invention.

Embodiments of the present invention can include a turbidity measuring device that can be implemented to reduce measurement uncertainty due to entrained air and/or other gases in a liquid sample by removing a significant portion of the entrained air and gases prior to an assay process. Typically, embodiments of the turbidity measuring device can include, but are not limited to, a fluidic module and a measurement module. The fluidic module can include a deaerator for removing entrained air and/or gases from a liquid sample. In one instance, the deaerator can be a combination of components or a sub-assembly of the fluidic module. When a liquid sample containing entrained gases is assayed, the gases can mimic the optical phenomenon of absorption, scatter, or fluorescence upon interrogation of the liquid sample by a beam of light, which can be deleterious to the assay process. The fluidic module can include the deaerator to minimize and/or remove entrained gasses in a liquid sample prior to the liquid sample being interrogated by the measurement module.

Generally, the deaerator can be implemented to separate entrained gases from a liquid in a continuous flow prior to an assay of the liquid. In one instance, the deaerator can separate entrained gases by encouraging a formation of small bubbles upon nucleation sites. In another instance, the deaerator can separate entrained gases by scavenging bubbles entrained in the liquid upon nucleated bubbles to form bubbles of increased size and then drawing the larger bubbles from the nucleation sites into an upward flow of liquid vented to atmosphere.

In one embodiment, to more fully ensure the removal of a significant portion of entrained gases, the fluidic module can re-circulate small bubbles of the entrained gases through the deaerator while liquid possessing an acceptably low level of entrained gas flows to an assay chamber. As can be appreciated, the turbidity measuring device can be configured to ensure that a liquid sample does not circumvent assay.

In one embodiment, the deaerator can include, but is not limited to, a plurality of lateral conic surfaces, a plurality of cylindrical surfaces, and a plurality of planar surfaces. Typically, the lateral conic surfaces can each include a helical structure proximate a base of the lateral conic surface. Each of the previously mentioned surfaces and structures can be implemented to facilitate a flow of a liquid sample through the deaerator. In some instances, the previously mentioned surfaces and structures can permit a construction of the fluidic module that can be compact in size and low in volume relative to an overall size of the turbidity measuring device.

Typically, a flow pattern encouraging immobilized bubbles to assimilate entrained air and/or gas from a liquid flow can be implemented with the deaerator. The recursive action created by a structure of the deaerator can recirculate buoyant components of a liquid sample (e.g. bubbles of air or other gas) through the deaerator until the bubbles have increased to a size sufficient to burst upon a surface of the liquid sample in an equalization chamber.

In one embodiment, the turbidity measuring device can include an inlet port, a first chamber, a first passage, a second passage, a surface, a second chamber, and an outlet port. The inlet port can be implemented for ingress of a liquid into the turbidity measuring device. The first chamber can be implemented for forming an interface between the liquid and atmosphere to vent gas carried by the liquid to atmosphere. The first passage can be implemented to act upon an upward flow of the liquid to increase a velocity of the liquid past one or more rounded helical surfaces cut into a directix of a conical cavity. The first passage can urge bubbles into an upward flow of the liquid. The second passage can be implemented to separate two bodies along which one or more cavities in opposing faces of the two bodies act upon a downward flow of the liquid entrained with gas to coalesce the gas to bubbles within the cavities. The surface can contain nucleated bubbles upon which the liquid entrained with gas flows to remove bubbles from the liquid. The second chamber can act on the liquid to separate buoyant bubbles of entrained gas from a downward, low velocity, flow of the liquid. The outlet port can be implemented for an egress of the liquid from the turbidity measuring device.

Another embodiment of the turbidity measuring device can include each component of the previously mentioned turbidity measuring device, and can further include a third chamber, a fourth chamber, an illumination means, and a detector means. The third chamber can be implemented as an assay chamber where a determination of one of more properties of a liquid can be made. The fourth chamber can be implemented as a waste chamber where a determination of flow can be made. The illumination means can be implemented to produce a light beam emitted by a light source. The beam can be implemented to irradiate the liquid. The detector means can be implemented to measure a phenomenon result from an interaction of the beam of light with the liquid.

Yet another embodiment of the turbidity measuring device can include each component of the previously mentioned turbidity measuring device, but the detector means can be implemented to measure scattered light from an interaction of the beam of light with the liquid.

Terminology

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning either or both.

References in the specification to "one embodiment", "an embodiment", "another embodiment, "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct physical connection between the identified elements, components, or objects. Often the manner of the coupling will be related specifically to the manner in which the two coupled elements interact.

The term "directly coupled" or "coupled directly," as used in this specification and appended claims, refers to a physical connection between identified elements, components, or objects, in which no other element, component, or object resides between those identified as being directly coupled.

The term "approximately," as used in this specification and appended claims, refers to plus or minus 10% of the value given.

The term "about," as used in this specification and appended claims, refers to plus or minus 20% of the value given.

The terms "generally" and "substantially," as used in this specification and appended claims, mean mostly, or for the most part.

Directional and/or relationary terms such as, but not limited to, left, right, nadir, apex, top, bottom, vertical, horizontal, back, front and lateral are relative to each other and are dependent on the specific orientation of a applicable element or article, and are used accordingly to aid in the description of the various embodiments and are not necessarily intended to be construed as limiting.

An Embodiment of a Turbidity Measuring Device

Figure 2:
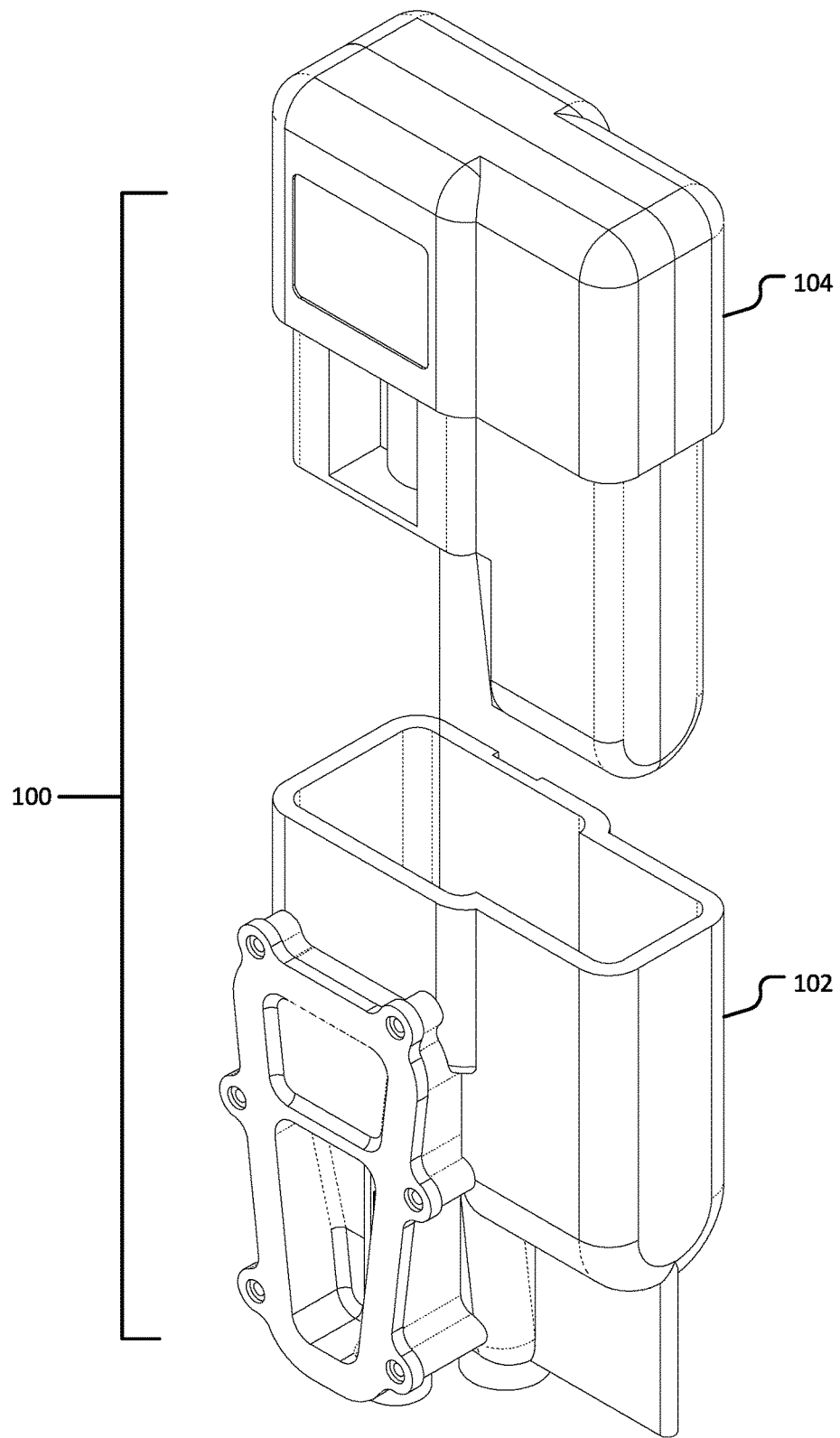
FIG. 2 is an isometric exploded view of a turbidity measuring device including a measurement module and a fluidic module according to one embodiment of the present invention.

Referring to FIGS. 1-2, detailed diagrams of an embodiment 100 of a turbidity measuring device 100 are illustrated. The turbidity measuring device 100 can be implemented as, but is not limited to, a turbidimeter, a fluorometer, and a nephelometer. For brevity, the turbidity measuring device 100 will be referred to as a turbidimeter hereinafter. Typically, the turbidimeter 100 can be implemented to measure the turbidity of a fluid. The turbidimeter 100 can include a deaerating path for a fluid to follow when passed through the turbidimeter 100.

In one embodiment, the turbidimeter 100 can include a fluidic module 102 and a measurement module 104, as shown in FIG. 2. The turbidimeter 100 can generally be implemented to interrogate a liquid with a beam of light and measure an amount of scattered light in relation to a particle content of a sample of the liquid contained within the fluidic module 102 by means of the measurement module 104.

Figure 3:
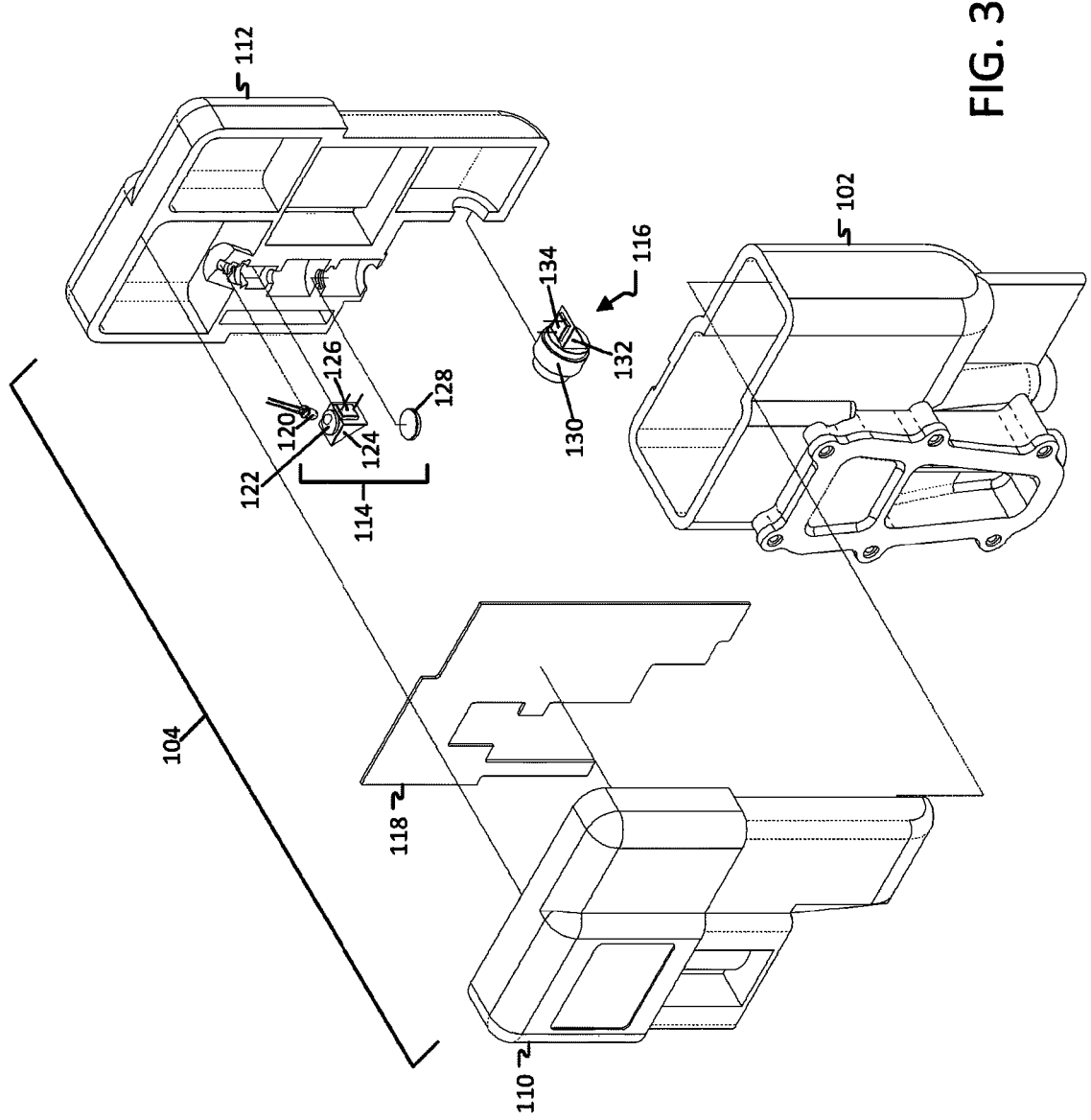
FIG. 3 is an isometric exploded view of a measurement module of a turbidity measuring device according to one embodiment of the present invention.

Referring to FIG. 3, an exploded view of the measurement module 104 is illustrated. The measurement module 104 can include, but is not limited to, a front housing 110, a rear housing 112, an illumination apparatus 114, a detection apparatus 116, and a printed circuit assembly 118. Generally, the front housing 110 and the rear housing can be fixed in relation with the illumination apparatus 114, the detection apparatus 116, and the printed circuit assembly 118 located there between, as shown in FIG. 3. The illumination apparatus 114 and the detection apparatus 116 can be held in relation preferentially for nephelometric assay substantially at 90 degrees per the geometry specified by the US Environmental Protection Agency (USEPA) publication 180.1 and to the geometry specified by ISO 7027-1999 standard for, "Water Quality—Determination of Turbidity".

As shown, the measurement module 104 can be configured to nest within the fluidic module 102. When the measurement module 104 is assembled with the fluidic module 102, the turbidimeter 100 can be in an operating configuration. In an operating configuration, the detection apparatus 116 can be configured to be immersed within a liquid and the illumination apparatus 114 can project a beam of light, or other invisible beam of electromagnetic radiation, into the liquid sample from above a surface of the liquid.

Still referring to FIG. 3, the illumination apparatus 114 can typically include, but is not limited to, an emitting source 120, a plano-convex lens 122, a right angle prism 124, a first detector 126, and a field lens 128. Light emitted from the emitting source 120 can be substantially shaped into a beam by the plano-convex lens 122. The beam can be configured to fall incident upon a hypotenuse of the right angle prism 124. When the beam falls incident upon the hypotenuse surface of right angle prism 124, the beam can be partially reflected and otherwise refracted at the hypotenuse surface. The refracted portion of the beam propagating from the hypotenuse surface of the right angle prism 124 can be adjusted by the field lens 128 to modify a divergence of the beam and/or focus the beam to within a view of the detection apparatus 116. The first detector 126 can be positioned upon one base of the right angle prism 124 to receive the partially reflected portion of the beam formed by the plano-convex lens 122. For instance, the plano-convex lens 122 can be positioned at a substantially right angle to the first detector 126 upon a second base of the right angle prism 124. In one embodiment, the plano-convex lens 122 and the first detector 126 can be coupled to the right angle prism 124 by an optical epoxy. In one example, the optical epoxy can be Epoxy Technology no. 301-2.

In one embodiment, the detection apparatus 116 can include, but is not limited to, a collection lens 130, a right angle prism 132, and a second detector 134. The detection apparatus 116 can be implemented to collect and convert light into an electrical response. As can be appreciated, scattered light may result from an interaction of the beam propagating from the field lens 128 of the illuminator apparatus 114 with a liquid sample contained within the fluidic module 102. The collection lens 130 can receive light scattered by the liquid sample substantially at 90 degrees from the beam propagating from the field lens 128. Light collected by the collection lens 130 can focus light scattered by the liquid sample through the right angle prism 132 to impinge upon the second detector 134. Electrical communication can be made between to the emitting source 120 and the first and second detectors 126, 134 through the printed circuit assembly 118.

As can be appreciated, the amount of light received by the collection lens 130 is dependent upon an intensity of the beam transmitted through the liquid sample and scatter characteristics of the liquid sample. Independent determination can be made for the transmitted beam energy by the first detector 126 and the scattered energy by the second detector 134. With the beam energy accounted for by incident beam first detector 126, additional changes in the energy determined by scattered light second detector 134 are therefore related to the particle content or scatter characteristics of the sample. For instance, this would apply for a non-absorptive liquid sample like water. Because entrained air or other gases present in the liquid sample scatter light with similar vigor as particulate matter present in the liquid sample, entrained air or gas bubbles act as interferences and therefore should be removed as much as possible prior to assay.

Figure 4:
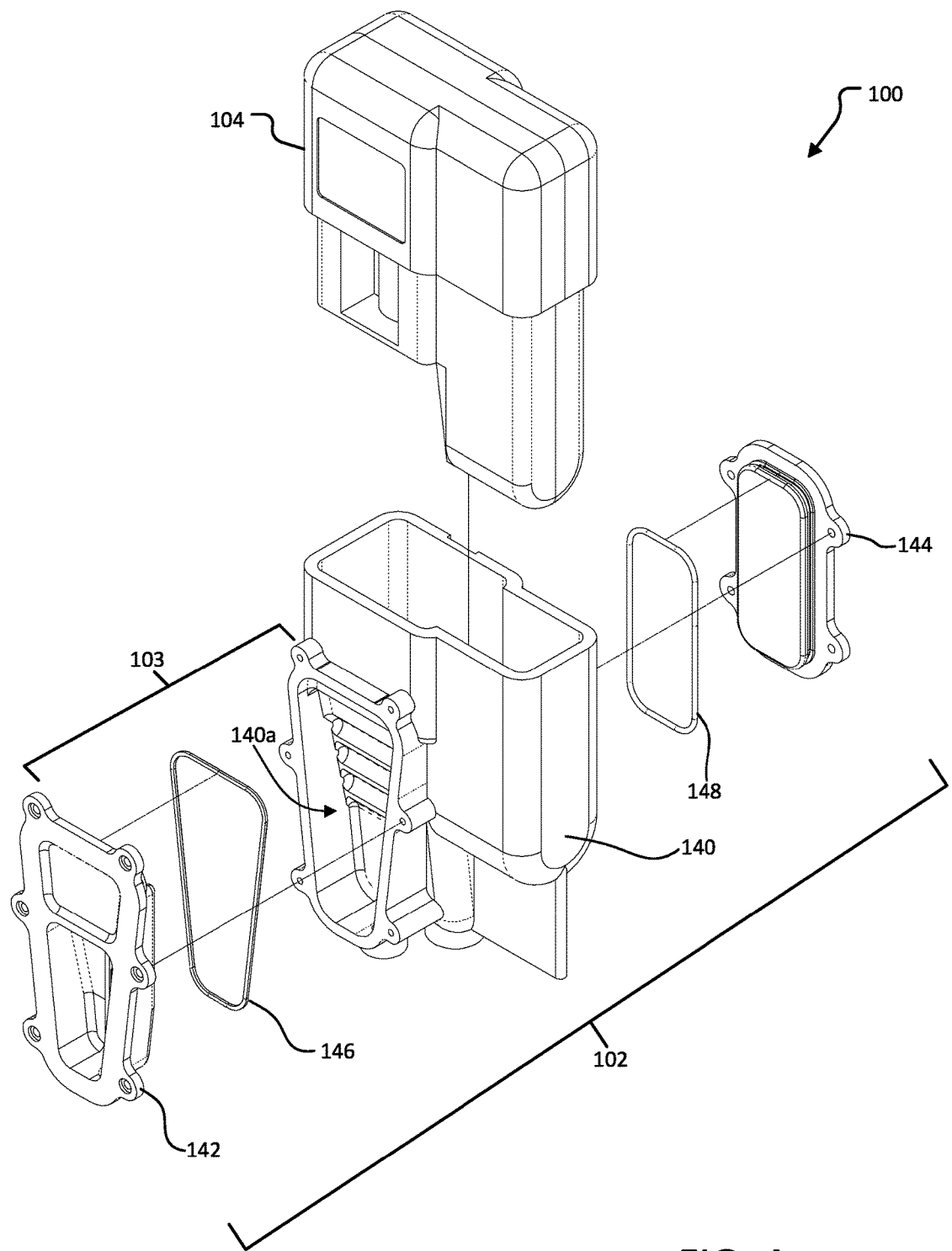
FIG. 4 is an isometric exploded view of a fluidic module of a turbidity measuring device according to one embodiment of the present invention.

Referring to FIG. 4, an exploded view of the fluidic module 102 is illustrated. As shown, the fluidic module 102 can include, but is not limited to, a flow body 140, a flow guide 142, an outlet cover 144, a flow guide seal 146, and an outlet cover seal 148. Generally, the fluidic module 102 can include a deaerator to remove entrained air or gas bubbles from the liquid sample being assayed. For instance, a sub-assembly 103 of the fluidic module 102 can be implemented to deaerate a liquid sample. The sub-assembly 103 can generally include a flow cavity 140a of the flow body 140, the flow guide 142, and the flow guide seal 146. Hereinafter, the sub-assembly 103 will be referred to as the deaerator. As shown in FIG. 4, an interior side of the flow guide 142 can be partially inserted into the flow cavity 140a of the flow body 140. Stated alternatively, the flow cavity 140a can be configured to receive and mate with the flow guide 142.

The flow cavity 140a and the flow guide 142 can act upon the liquid sample flowing through the fluidic module 102 to remove entrained air without significantly altering a particulate matter content of the liquid sample. The flow guide seal 146 can prevent liquid from escaping between the flow cavity 140a and the flow guide 142. Similarly, the outlet cover seal 148 can prevent liquid from escaping between the flow body 140 and the outlet cover 144. As can be appreciated, a function of the flow guide 142 in concert with the adjacent portion of the flow cavity 140a can be to route liquid and to control the distribution and flow patterns of the liquid within various elements of the turbidimeter 100.

Figure 5:
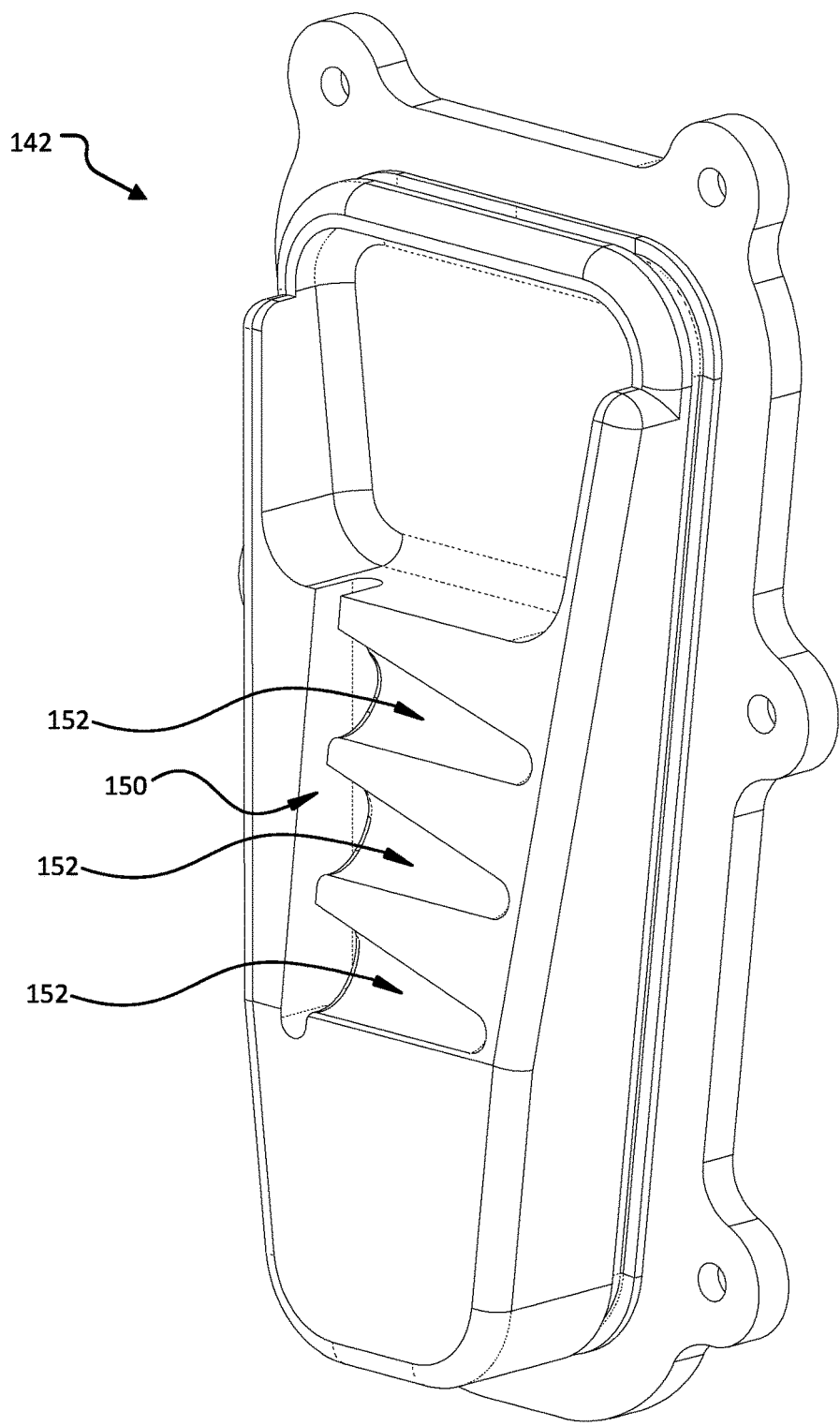
FIG. 5 is an isometric view of a flow guide according to one embodiment of the present invention.
Figure 6:
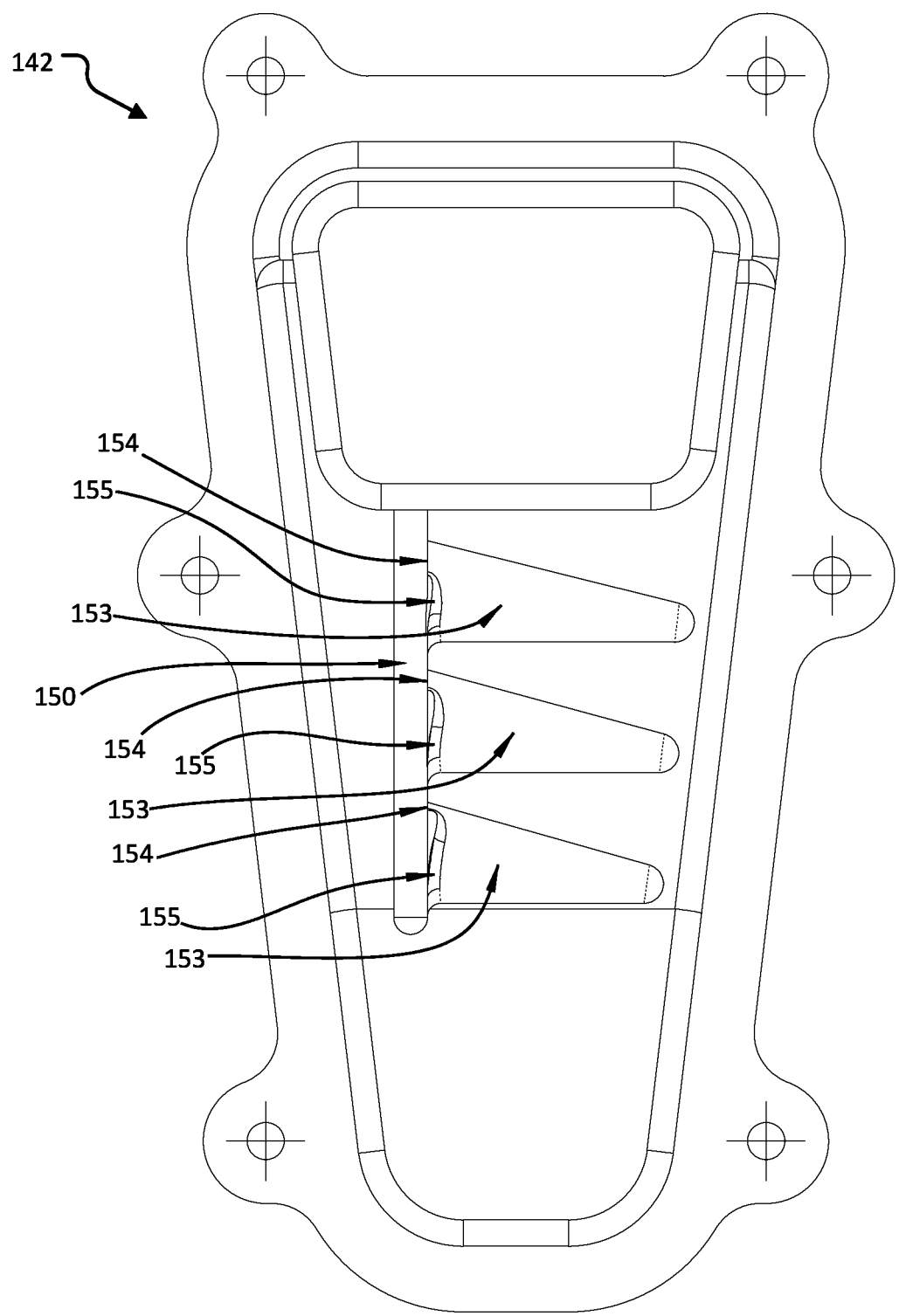
FIG. 6 is a front view of a flow guide according to one embodiment of the present invention.

Referring to FIGS. 5-6, detailed diagrams of the flow guide 142 are illustrated. The flow guide 142 can generally include, but is not limited to, a first flow passage 150 and a plurality of half-conical shaped depressions 152. Generally, the flow guide 142 can direct a flow of liquid upwardly within the first flow passage 150 along the plurality of half-conical shaped depressions 152. As shown in FIG. 6, the plurality of half-conical shaped depressions 152 can each include a lateral conic surface 153. As shown, the lateral conic surfaces 153 can each terminate at the first flow passage 150. Generally, the lateral conic surfaces 153 can each terminate at a substantially oblique angle slanting gently upwardly towards the first flow passage 150, as best shown in FIG. 6. In one instance, the lateral conic surfaces 153 can terminate along the first flow passage 150 at a substantially oblique angle as defined by an elliptical cone perpendicular to the first flow passage 150.

In one embodiment, each of the plurality of half-conical shaped depressions 152 can include a directrixes 154, or a base edge, located proximate the first flow passage 150. Each of the directrixes 154 can be partially modified with a rounded at least partially helical structure 155. The rounded at least partially helical structures 155 can extend into the lateral conic surfaces 153 of each of the plurality of half-conical shaped depressions 152.

Figure 7:
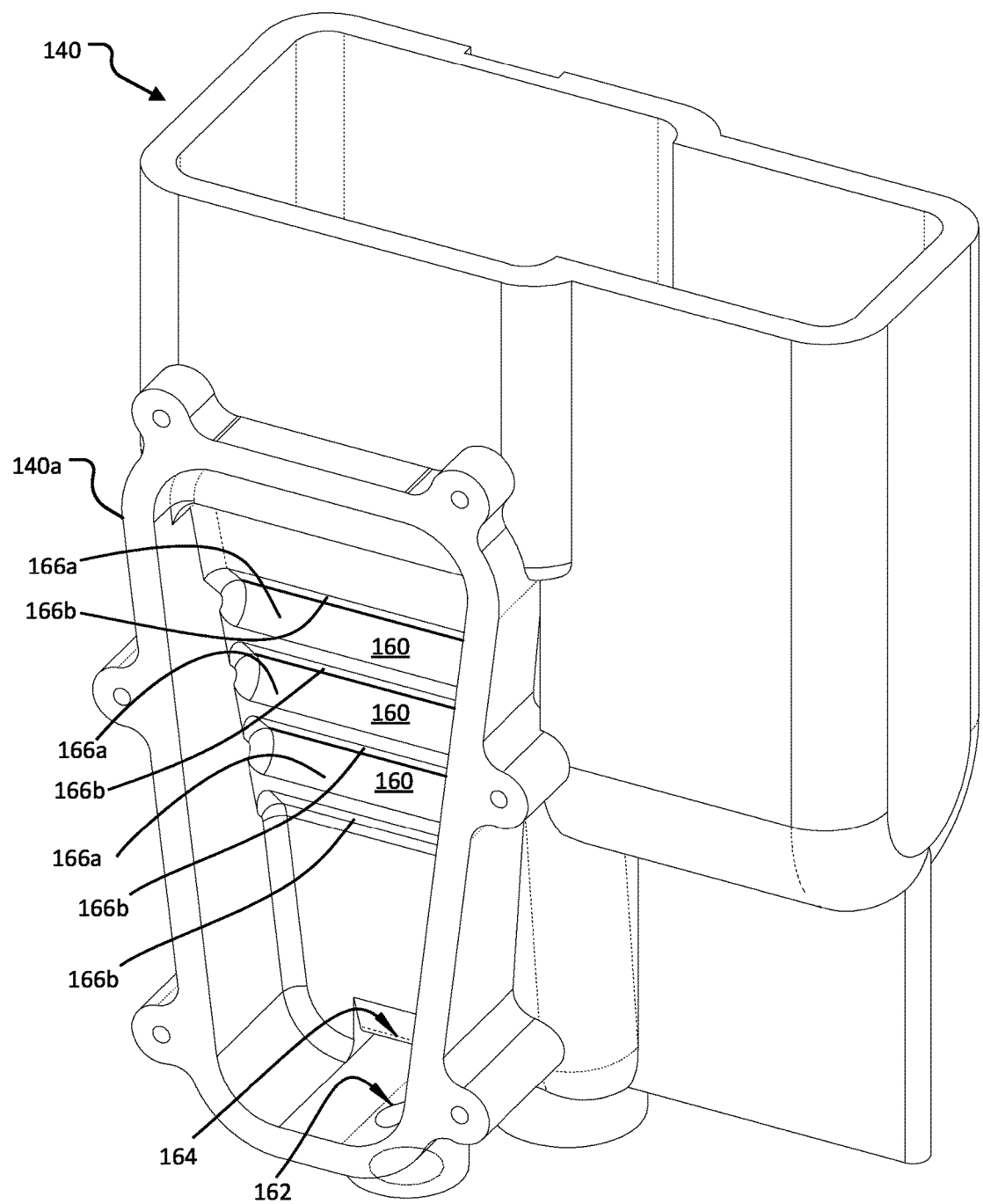
FIG. 7 is an isometric view of a flow body of a turbidity measuring device according to one embodiment of the present invention.
Figure 9A:
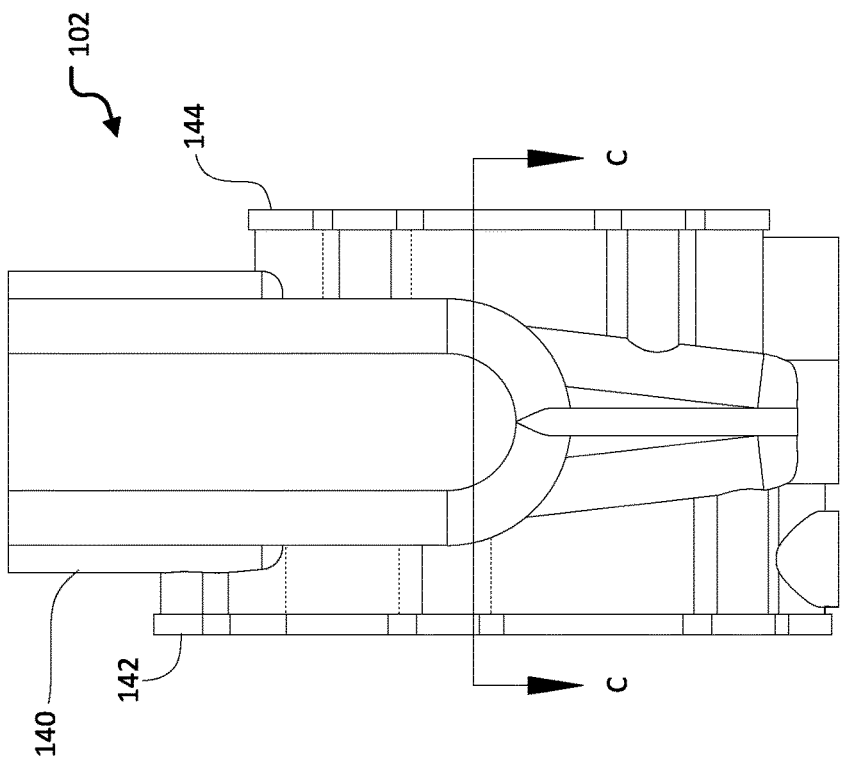
FIG. 9A is a side view of a turbidity measuring device showing cross-section line C-C according to one embodiment of the present invention.
Figure 8A:
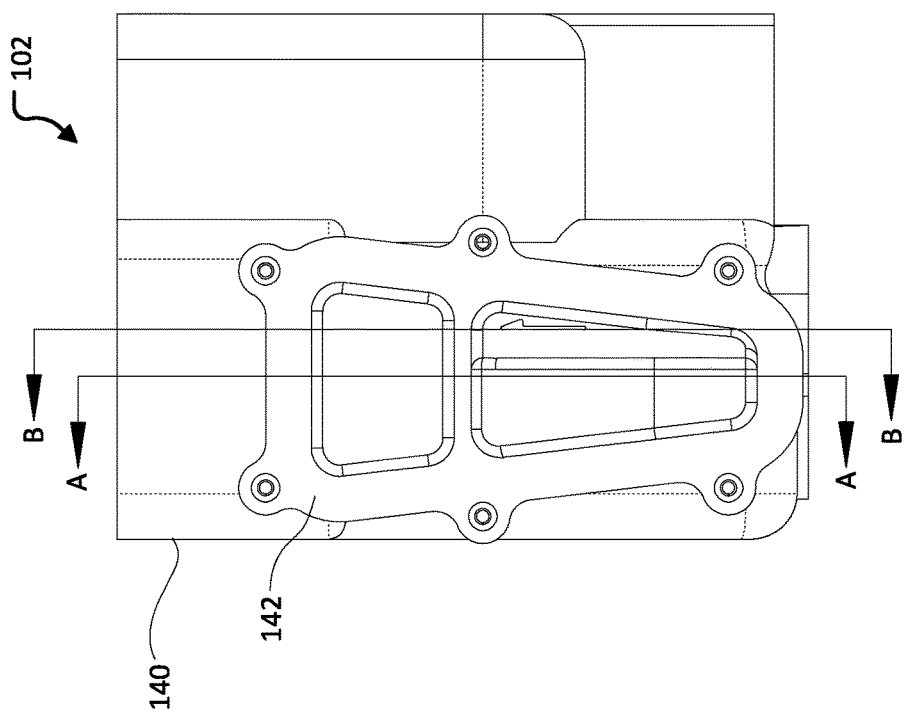
FIG. 8A is a front view of a flow assembly of a turbidity measuring device showing cross-section lines A-A and B-B according to one embodiment of the present invention.
Figure 8B:
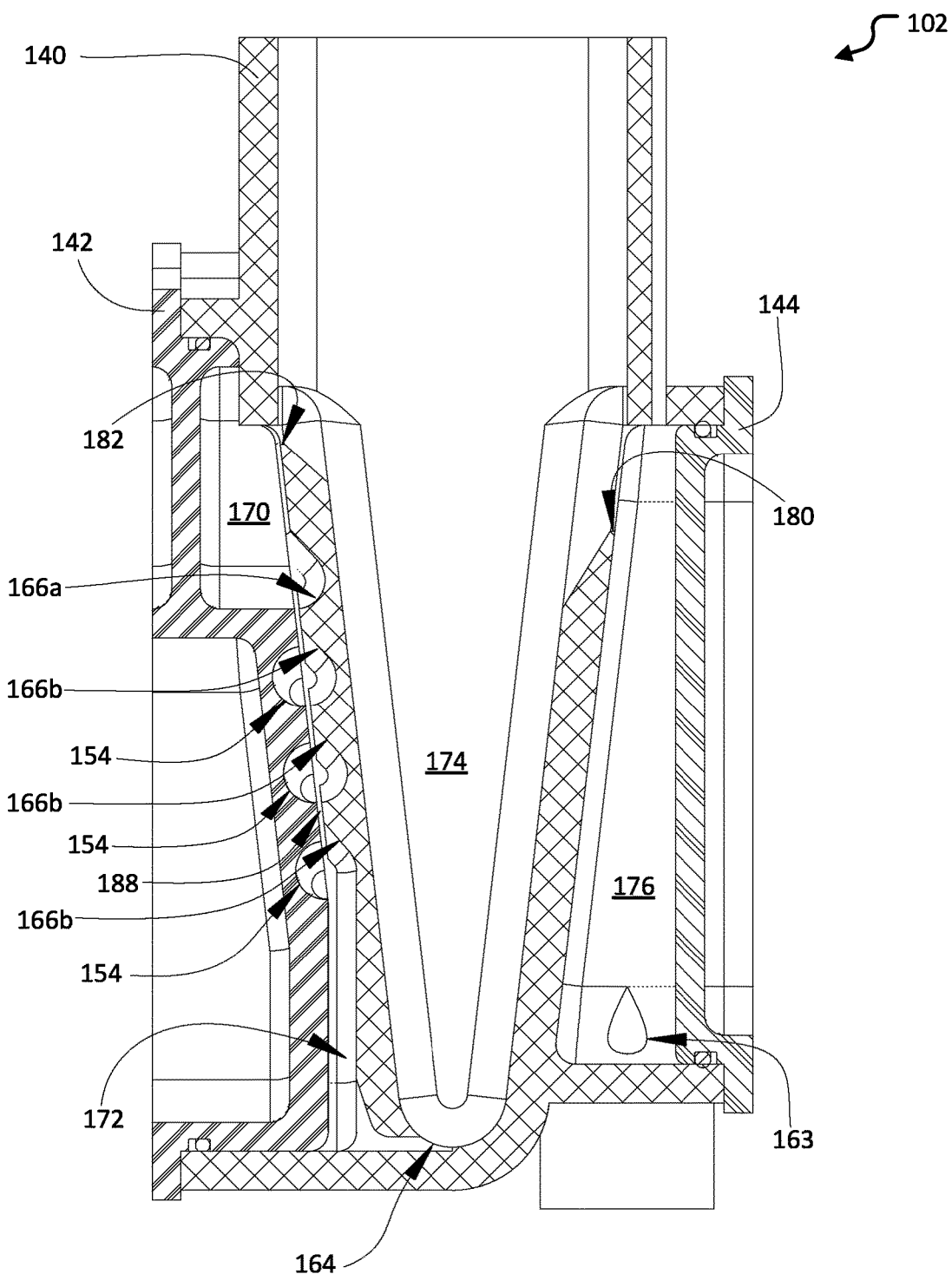
FIG. 8B is a cross-section view taken along line A-A in FIG. 8A of the flow assembly showing liquid handling structures according to one embodiment of the present invention.
Figure 8C:
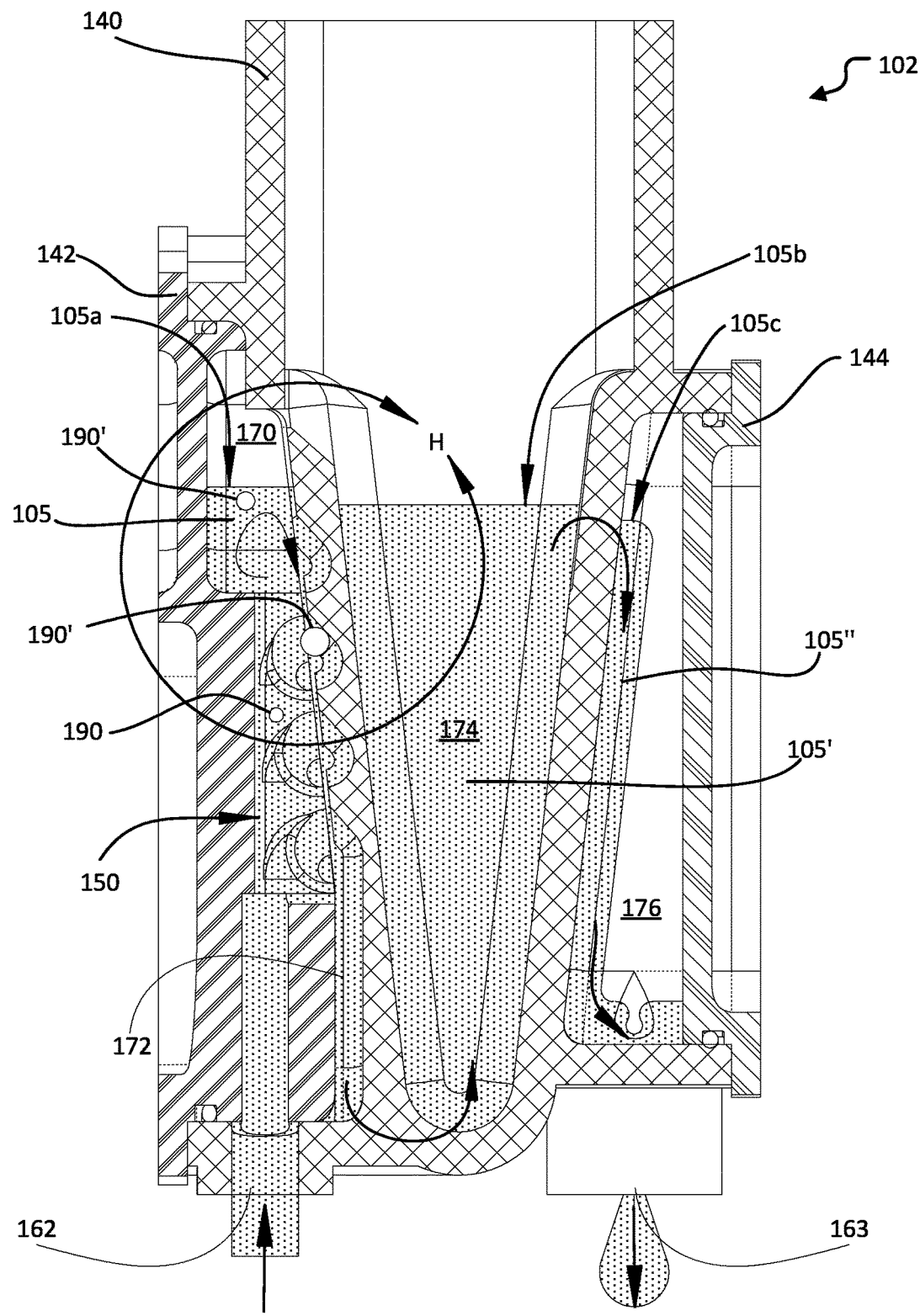
FIG. 8C is a cross-section view taken along line B-B in FIG. 8A of the turbidity measuring device illustrating several structures of the device that act upon a liquid sample to remove entrained air and other gases as the liquid flows there though according to one embodiment of the present invention.
Figure 8D:
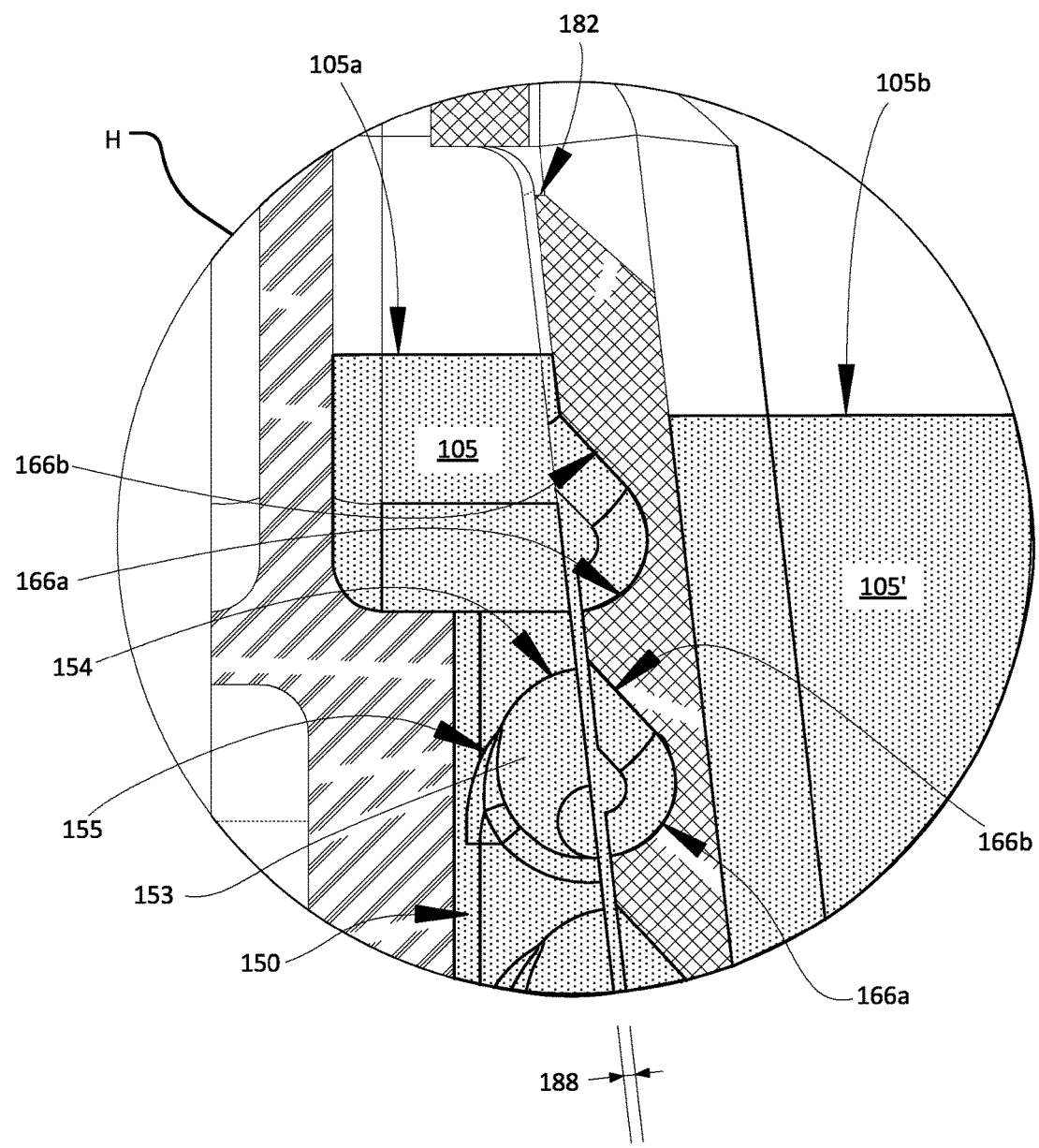
FIG. 8D is a detail view of H from FIG. 8C of a flow guide and a flow body assembly according to one embodiment of the present invention.

Referring to FIGS. 7-8D, detailed diagrams of the flow body 140 and flow cavity 140a are illustrated. Typically, the flow cavity 140a can include a plurality of half-cylindrical shaped depressions 160, an inlet port 162, and a third flow passage 164. As shown in FIGS. 7 and 8B-8D, the plurality of half-cylindrical shaped depressions 160 can each include a surface defined by a quarter cylindrical surface 166a mated to a planar surface 166b. Typically, the planar surface 166b can be positioned tangential to the cylindrical surface 166a and slope upwardly within an area substantially adjacent to the corresponding conic surfaces 153 of the flow guide 142 when the flow guide 142 is coupled to the flow cavity 140a. As can be appreciated, when the flow guide 142 is coupled to the flow cavity 140a, the deaerator 103 can be formed. The quarter cylindrical surfaces 166a and the planar surfaces 166b of the flow cavity 140a can generally be seen in FIGS. 7-8D.

Referring to FIG. 8A, cross-sectional lines A-A and B-B are shown on the turbidimeter 100. FIG. 8B, showing a cross-section view along the line A-A of FIG. 8A, and FIG. 8C, showing a cross-section view along the line B-B, illustrate various chambers and passages of the fluidic module 102.

As shown generally in FIGS. 8A-8D, the fluidic module 102 can include, but is not limited to, a first chamber 170, a second chamber 172, a third chamber 174, and a fourth chamber 176. The first chamber 170 can be an equalization chamber, the second chamber 172 can be a down-flow chamber, the third chamber 174 can be an assay chamber, and the fourth chamber 176 can be a waste chamber.

In one embodiment, a gap 188 can be provided between the flow guide 142 and the flow cavity 140a. Generally, the gap 188 can create a second flow passage between the equalization chamber 170 and the down-flow chamber 172 through the deaerator 103. In one instance, the semi-conical depressions 152 and the semi-cylindrical depressions 160, shown in FIGS. 5-7, can be offset when the flow guide 142 is coupled to the flow cavity 140a. For example, respective top and bottom edges of the semi-conical depressions 152 and the semi-cylindrical depressions 160 can be separated by a small gap through which a liquid can flow into the down-flow chamber 172 from the equalization chamber 170.

The third flow passage 164 can fluidly connect the down-flow chamber 172 to the assay chamber 174 enabling a substantially bubble-free liquid sample to flow into the assay chamber 174. As can be appreciated, the assay chamber 174 can receive the measurement module 104 for performing an assay of a liquid being passed through the fluidic module 102.

In one embodiment, the fluidic module 102 can include a first weir or spillway 180 and a second weir or spillway 182, as shown in FIG. 8B. The first weir 180 can be a waste weir and the second weir 182 can be an overflow weir. The waste weir 180 can connect the assay chamber 174 to the waste chamber 176. As can be appreciated, the waste weir 180 can create a fourth flow passage for liquids in the assay chamber 174 to flow into the waste chamber 176.

As shown in FIG. 8B, the overflow weir 182 can connect the equalization chamber 170 with the assay chamber 174. The overflow weir 182 can be implemented to enable the liquid sample to flow from the equalization chamber 170 through the assay chamber 174 to the waste chamber 176 in the event a flow capacity of the deaerator 103 is exceeded or there is an obstruction within the deaerator 103. For instance, if there is an obstruction within the down-flow chamber 172 or the third flow passage 164 that can prevent normal flow of the liquid sample through fluidic module 102.

Gases liberated from the liquid sample by the deaerator 103 can be vented to atmosphere through an opening above the overflow weir 182 to the assay chamber 174. Typically, the gases can be vented to an atmosphere above a fluid level within the assay chamber 174. The waste chamber 176 can be vented to atmosphere through an opening above the waste weir 180 located approximate a top of the waste chamber 176.

Figure 9B:
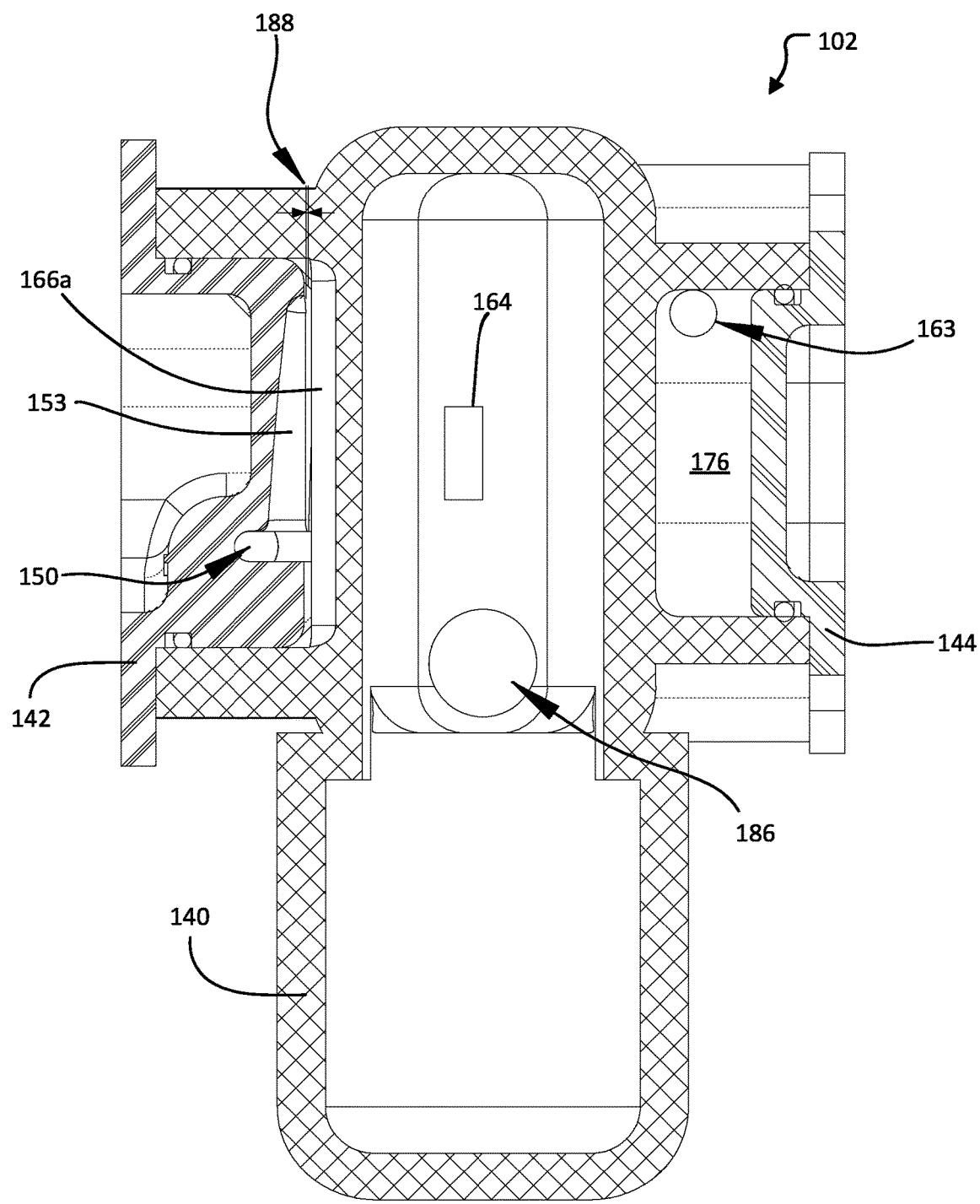
FIG. 9B is cross-section view taken along line C-C of FIG. 9A showing a longitudinal extent of a deaerator structure according to one embodiment of the present invention.
Figure 10:
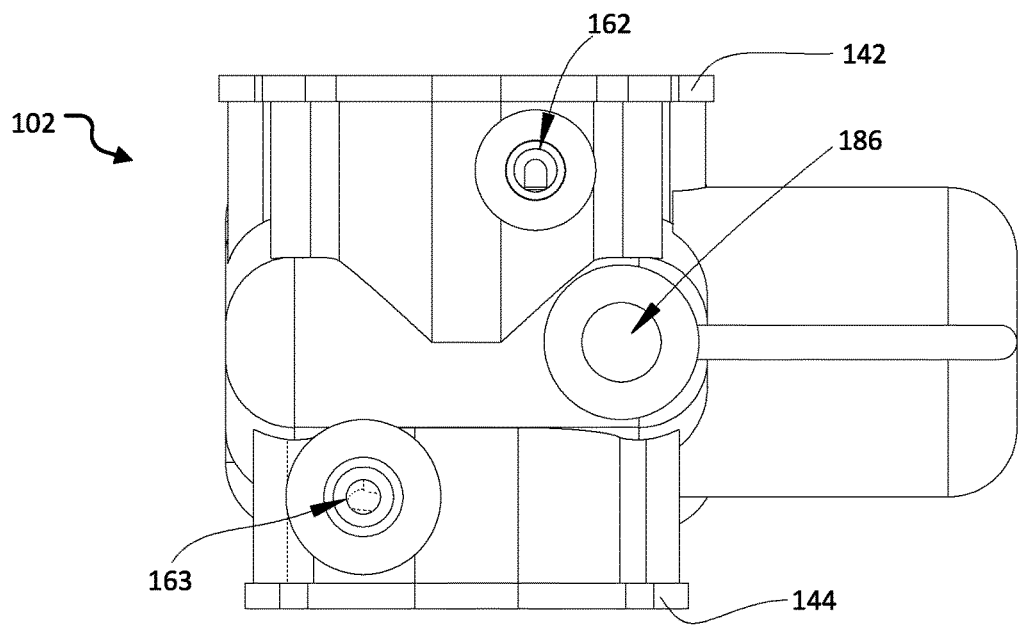
FIG. 10 is a bottom view of a turbidity measuring device according to one embodiment of the present invention.
Figure 11:
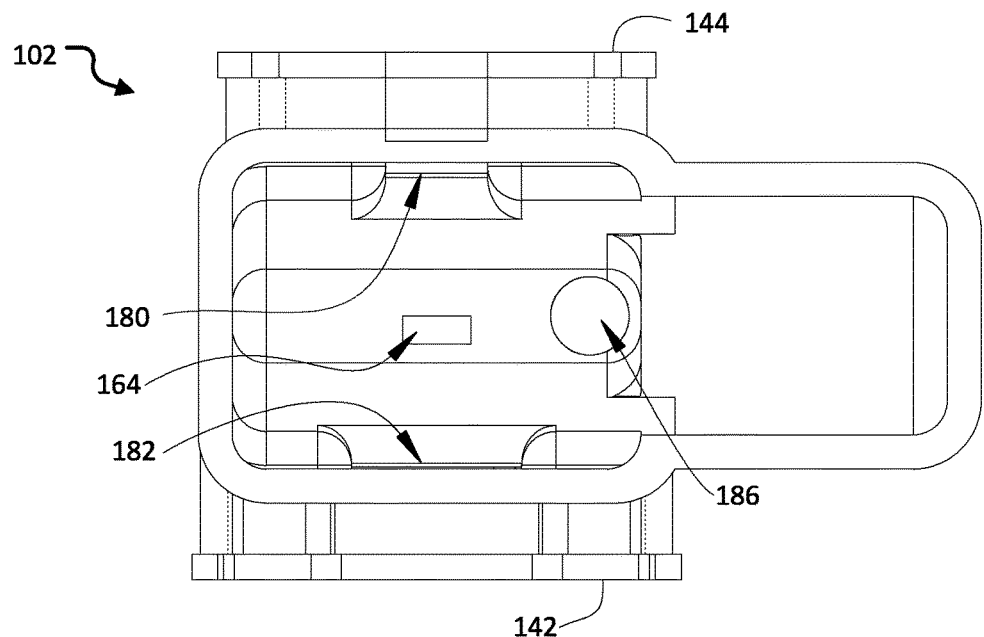
FIG. 11 is a top view of a turbidity measuring device according to one embodiment of the present invention.
Figure 12:
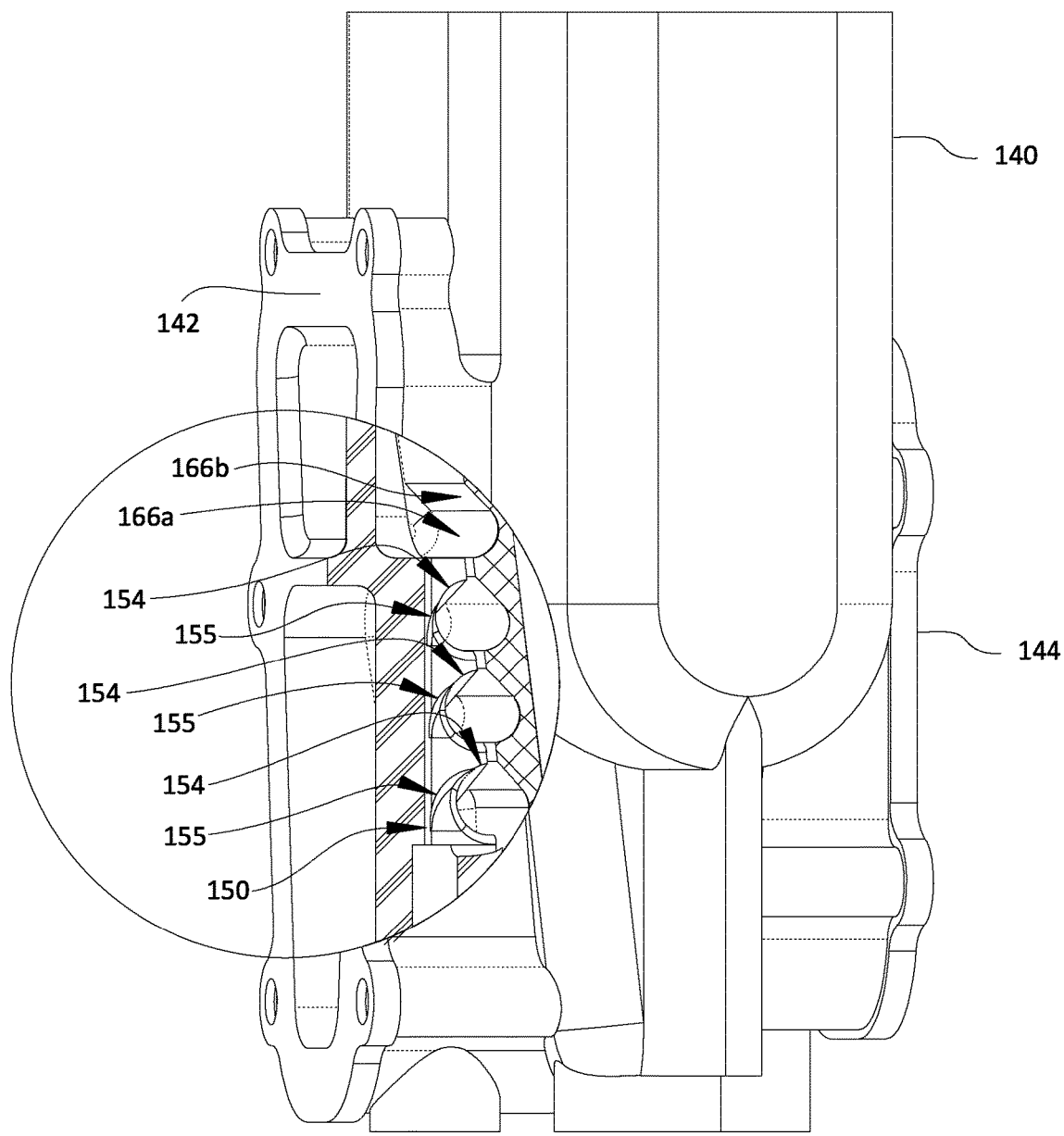
FIG. 12 is a broken-out view of a gas accumulator structure formed by a flow guide and a flow body of a turbidity measuring device according to one embodiment of the present invention.

Typically, the fluidic module 102 can include a drain port 186 located approximate a bottom portion of the assay chamber 174, as shown in FIG. 9B, FIG. 10 and FIG. 11. The drain port 186 can be closed during normal operation. The drain port 186 can typically be opened or closed as needed when the liquid sample contained within the fluidic module 102 is drained for service or replaced with a known analytic value of liquid sample. For instance, a standard of known concentration or constituent of an analyte of interest can be a liquid sample having a known analytic value.

Referring back to FIG. 8C, a flow of a liquid sample through the deaerator 103 is illustrated to show the process of removing air or other entrained gases from a liquid 105. It is to be appreciated that some elements referenced in one or several of the FIGS. 5-8D may not be referenced in each figure, but are nonetheless present in each figure.

In a typical implementation, the liquid 105 can enter the turbidimeter 100 at the bottom of the flow body 140 through the inlet port 162. The flow guide 142 can restrict the liquid 105 to flow upwardly within the first flow passage 150 and then terminate in the equalization chamber 170. The restriction within the first flow passage 150 as compared to the diameter of the inlet port 162 can increase a velocity of the liquid 105 within the first flow passage 150.

The plurality of half-conical depressions 152 and the plurality of half-cylindrical depressions 160 can be implemented as interferences for the liquid 105. As can be seen, larger gas bubbles 190' present in the liquid 105 can be provided an unobstructed path along the first flow passage 150 to the equalization chamber 170 and a liquid surface 105a upon which the larger bubbles 190' can burst and are vented to atmosphere. The plurality of partially rounded helical structures 155, as shown in FIG. 8D, can act to divert a portion of the upward liquid 105 flow impinging on the helical surfaces. The diverted portion of the liquid 105 can be directed to flow along the lateral conic surfaces 153 and the plurality of half-cylindrical shaped depressions 160 creating a backwash. The backwash can be directed to the interferences 152, 160 and help to dislodge any bubbles accumulated on the interferences 152, 160. The dislodged bubbles can typically be swept into the first flow passage 150 whereupon the bubbles are carried to the equalization chamber 170 to burst on the liquid surface 105a and be vented to atmosphere.

The diverted portion of the liquid 105 can typically recirculate through the deaerator 103 and pass through to the assay chamber 174. As such, the liquid 105 can eventually pass through to the assay chamber 174 even when being diverted and/or recirculated through the deaerator. As can be appreciated, a design of the deaerator 103 can ensure that substantially all liquid entering the turbidimeter 100 can be passed through to the assay chamber 174. A lateral liquid flow created by the portion of the liquid flow diverted by the plurality of partially rounded helical structures 155 can assist in preventing bubbles form traveling downwardly between successive half-conical depressions 152.

The liquid 105 flowing through the first flow passage 150 and across the directrixes 154 can create a region of reduced pressure within the first flow passage 150 that thereby urge (or pull) bubbles coalesced between the flow guide 142 and the planar surfaces 166b of the flow body 140 into the upward liquid flow within the first flow passage 150. Upon reaching the equalization chamber 170, the liquid 105 can be given no option other than to flow downward within the gap 188 between an interior face of the flow guide 142 and the flow cavity 140a, as shown in FIGS. 8B-8D. In one embodiment, the gap 188 can be set to a distance of about 0.5 mm to 3.2 mm. In another embodiment, the gap 188 can set to a distance between about 0.1 mm to 4.0 mm.

Figure 13:
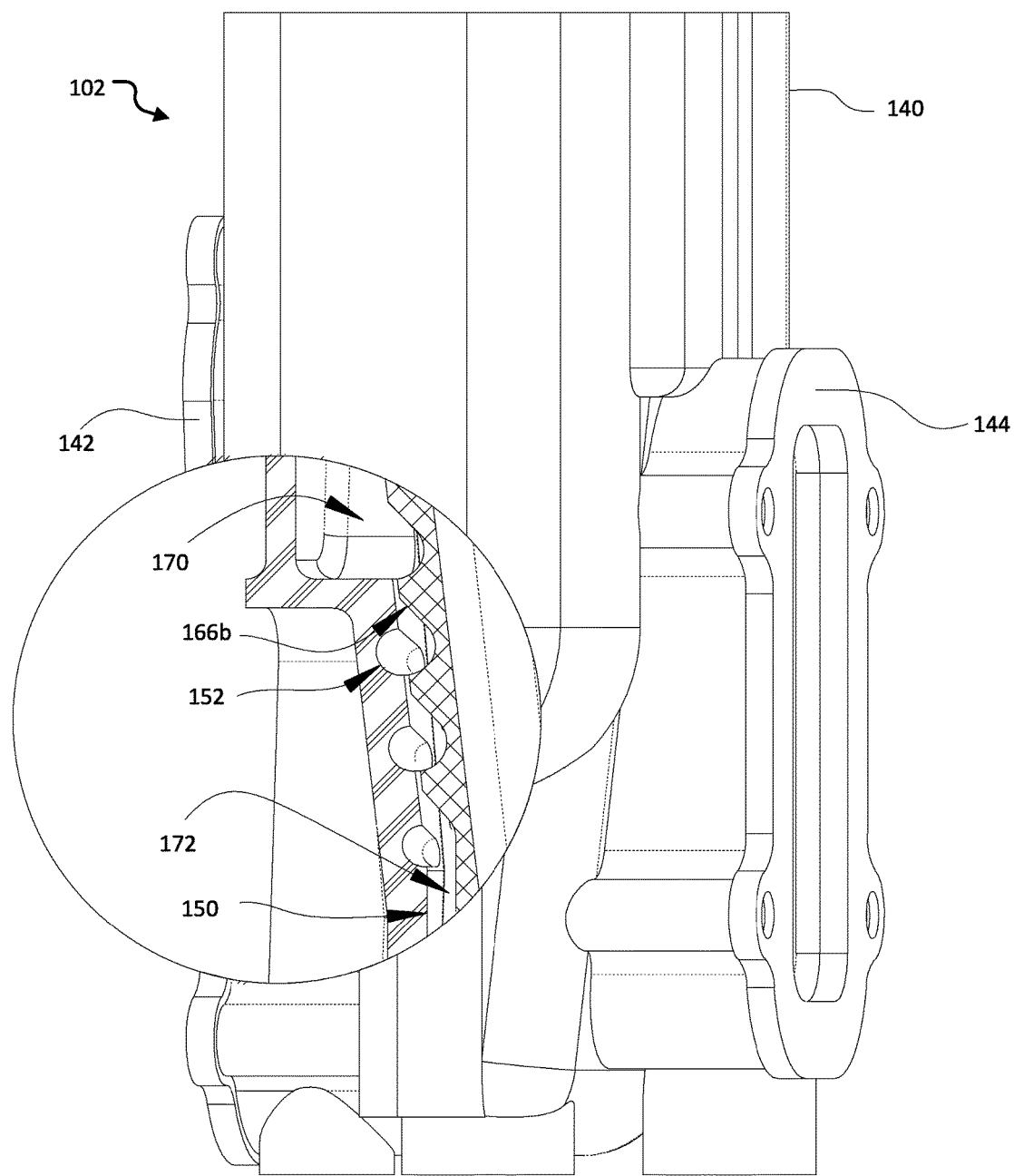
FIG. 13 is a broken-out view of a gas removal structure formed by a flow guide and a flow body of a turbidity measuring device at a vertical flow guide structure of the flow guide according to one embodiment of the present invention.

Small bubbles 190 of air or gas entrained in the liquid 105 can be encouraged to form along the sharp edge of the planar surfaces 166b of the flow cavity 140a where nucleation sites are prominent as the liquid 105 flows downwardly in the gap 188. The nucleated bubbles can typically grow to larger sizes along the sharp edges of the planar surfaces 166b while being captured by surface tension on an interior face of the flow guide 142 on the planar surfaces 166b of the flow cavity 140a, as shown generally in FIG. 8C and FIG. 13. Bubbles of air and/or gas can have a natural tendency to assimilate the smaller bubbles entrained in the liquid 105 as the liquid 105 flows from the equalization chamber 170 past immobilized bubbles to the down-flow chamber 172. As can be appreciated, this can result in a growth of the immobilized bubbles in the deaerator 103.

After the captured bubbles have grown to a sufficient size, or buoyancy, to overcome forces holding the bubbles to the planar surfaces 166b of the flow cavity 140a, the free-floating bubbles can be urged into the half-conical depressions 152 of the flow guide 142 due to backwash. Backwash can be created by an upward flow of the liquid 105 through the first flow passage 150 acting on the plurality of partially rounded helical structures 155, as previously described, and the downward flow of the liquid 105 from the equalization chamber 170 to the down-flow chamber 172. As a result, dislodged bubbles can be carried to the equalization chamber 170 along the first flow passage 150 by the upwardly flowing liquid 105, whereupon bubbles can burst on the liquid surface 105a and can be vented to atmosphere.

As shown in FIG. 8C, the de-aerated liquid 105' may flow downward in the down-flow chamber 172 where residual bubbles can be provided an opportunity to drift upwardly to the planar surfaces 166b upon which the fine bubbles can re-enter the deaerator 103 and can again be drawn to the upward liquid flow in the first flow passage 150. The de-aerated liquid 105' may flow through the third flow passage 164 into the bottom of the assay chamber 174 where a determination of composition or a property of interest of the liquid sample can be determined by the measurement module 104. As can be appreciated, other properties of the liquid sample may also be determinable to a greater accuracy without the presence of entrained air and/or other gases in the liquid sample using alternate or additional illumination and/or detection arrangements in communication with the de-aerated liquid 105' by optical or fluidic connection.

Of note, a volume of a liquid sample within the assay chamber 174 can be determined by a size and a shape of the assay chamber 174 and a height of the waste weir 180 above the third flow passage 164.

A surface 105b of the de-aerated liquid 105' can be level with or slightly higher than the waste weir 180 due to a surface tension along the weir. As a liquid flows from the inlet port 162 to an outlet port 163 of the fluidic module 102, the surface 105a of the liquid 105 within the equalization chamber 170 can be slightly higher than the de-aerated liquid surface 105b in the assay chamber 174 due to flow restriction (e.g., pressure drop) through the gap 188 between the interior face of the flow guide 142 and the flow cavity 140a. The gap distance 188 can be preferentially set to provide maximum de-aeration of the liquid 105 while minimizing a difference in height between the liquid surface 105a and the de-aerated liquid surface 105b for a given range of flow through the fluidic module 102. Sample flow of the preferred embodiment can be judicially selected based upon a flow characteristic of a liquid sample at operating conditions. For instance, a typical flowrate from 0.001 to 10 liters per minute (LPM) can be implemented.

The de-aerated liquid 105' can spill over the waste weir 180 into the waste chamber 176 to the outlet port 163 as a waste liquid 105". The waste chamber 176 can be useful in determining if liquid is flowing or not flowing through the fluidic module 102 as external light prevents otherwise and visual inspection is not possible while the turbidimeter 100 is in an operable configuration with the measurement module 104 coupled to the fluidic module 102. The outlet port 163 positioned approximate the bottom of the waste chamber 176 can be routed to an appropriate waste handling system for a given liquid sample composition.

In one example flow path, the liquid 105 can enter the turbidimeter 100 through the inlet port 162. The first flow passage 150 can take the liquid 105 from the inlet port 162 to the equalization chamber 170. From the equalization chamber 170, the liquid 105 can flow to the down-flow chamber 172 via the second flow passage created by the gap 188. From the down-flow chamber 172, the liquid 105 can flow to the assay chamber 174 via the third flow passage 164. As previously mentioned, the waste weir 180 can create the fourth flow passage for the liquid 105 to flow from the assay chamber 174 to the waste chamber 176. The liquid 105 can then exit the turbidimeter 100 through the outlet port 163.

Advantageously, embodiments of the deaerator 103 can be relatively compact in size and can include a relatively low volume. For instance, the deaerator 103 can be relatively small in proportion to the turbidimeter 100 as a whole.

Alternative Embodiments and Variations

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

I claim:

1. A turbidity measuring device comprising:
   a fluid passage including:
   a first passage taking a liquid from an inlet past one or more rounded helical surfaces to a first chamber; and
   a second passage taking the liquid from the first chamber past a plurality of opposing semi-conical depressions and semi-cylindrical depressions to a second chamber.

2. The turbidity measuring device of claim 1, wherein each of the rounded helical surfaces is cut into a directix of one of the plurality of semi-conical depressions.

3. The turbidity measuring device of claim 1, wherein the third chamber is an assay chamber and the fourth chamber is a waste chamber.

4. The turbidity measuring device of claim 1, wherein the plurality of opposing semi-conical depressions and semi-cylindrical depressions are offset.

5. The turbidity measuring device of claim 1, the device further comprising:
   a fluidic module including the fluid passage; and
   a measurement module removably inserted into the fluidic module, the measurement module including:
   an illumination module providing a beam of light; and
   a detection module for measuring scattered light.

6. The turbidity measuring device of claim 5, wherein the illumination module comprises:
   a light emitting device;
   a plano-convex lens;
   a right angle prism;
   a first detector; and
   a field lens.

7. The turbidity measuring device of claim 6, wherein the detection module comprises:
   a collection lens;
   a right angle prism; and
   a second detector.

8. The turbidity measuring device of claim 7, wherein the first detector is electrically connected to the second detector.

9. The turbidity measuring device of claim 5, wherein the fluidic module further includes:
   a flow body including the plurality of semi-cylindrical depressions, the flow body adapted to receive the measurement module; and
   a flow guide coupled to the flow body, the flow guide including the plurality of semi-conical depressions.

10. The turbidity measuring device of claim 9, wherein the fluidic module further includes:
    an outlet cover coupled to the flow body;
    a flow guide seal located between the flow guide and the flow body; and
    an outlet cover seal located between the outlet cover and the flow guide.

11. The turbidity measuring device of claim 1, wherein the device further includes a third passage taking the liquid from the second chamber to a third chamber.

12. The turbidity measuring device of claim 11, wherein the device further includes a fourth passage taking the liquid from the third chamber to a fourth chamber.

13. A turbidity measuring device comprising:
    a fluidic module, the fluidic module including:
    a flow body having a plurality of semi-cylindrical depressions; and
    a flow guide coupled to the flow body, the flow guide having a plurality of semi-conical depressions;
    a measurement module, the measurement module including:
    an illumination module providing a beam of light; and
    a detection module for measuring light;
    wherein (i) the plurality of semi-conical depressions and the plurality of semi-cylindrical depressions are opposed to one another, and (ii) the opposing plurality of semi-cylindrical depressions and semi-cylindrical depressions are offset in relation to one another.

14. The turbidity measuring device of claim 13, wherein the fluidic module further includes:
    an inlet port;
    a first chamber in fluid connection with the inlet port;
    a second chamber in fluid connection with the first chamber;
    a third chamber in fluid connection with the second chamber; and
    a fourth chamber in fluid connection with the third chamber.

15. The turbidity measuring device of claim 13, wherein the fluidic module includes a fluid passage, the fluid passage including:
    a first passage taking a liquid from the inlet port past one or more rounded helical surfaces to the first chamber; and
    a second passage taking the liquid from the first chamber past the plurality of opposing semi-conical depressions and semi-cylindrical depressions to the second chamber;
    a third passage taking the liquid from the second chamber to the third chamber; and
    a fourth passage taking the liquid from the third chamber to the fourth chamber.

16. A fluidic module comprising:
    a flow body including:
    a cavity;
    a first set of depressions located in the cavity, each of the first set of depressions having a cross-section defined by a quarter-cylindrical shape mated to a planar shape;
    a flow guide removably coupled to the flow body, the flow guide including:
    a second set of depressions, each of the second set of depressions having a cross-section defined by a half-conical shape;
    wherein the first set of depressions are located opposite the second set of depressions when the flow body is coupled to the flow guide.

17. A combination comprising:
    the fluidic module of claim 16; and
    a measurement module, the measurement module including:
    an illumination module providing a beam of light; and
    a detection module for measuring light.

18. The fluidic module of claim 16, wherein the first set of depressions are offset in relation to the second set of depressions when the flow body is coupled to the flow guide.

19. The fluidic module of claim 16, wherein the flow guide and the cavity of the flow body are separated between 0.5 mm to 3.2 mm when coupled together.

20. A device for measuring turbidity, the device comprising:
- a plurality of semi-cylindrical depressions;
- a plurality of semi-conical depressions opposing the plurality of semi-cylindrical depressions, the plurality of semi-conical depressions each including a rounded helical surface cut into a directix of the semi-conical depression; and
- a fluid passage, the fluid passage including:
    - a first passage taking a fluid from an inlet of the device past the rounded helical surfaces to a first chamber;
    - a second passage taking the fluid from the first chamber past the plurality of opposing semi-conical depressions and semi-cylindrical depressions to a second chamber.

21. The turbidity measuring device of claim 20, wherein the device further includes a third chamber fluidly connected to the second chamber.

22. The turbidity measuring device of claim 21, wherein an assay process is performed in the third chamber.

23. The turbidity measuring device of claim 22, wherein the device further includes:
- an illumination module providing a beam of light; and
- a detection module for measuring light.

* * * * *